(12) United States Patent
Rankin

(10) Patent No.: US 8,795,714 B2
(45) Date of Patent: *Aug. 5, 2014

(54) INTRA-MAMMARY TEAT SEALANT FORMULATION AND METHOD OF USING SAME TO REDUCE OR ELIMINATE VISUAL DEFECTS IN AGED CHEESES

(75) Inventor: Scott A. Rankin, Cross Plains, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 300 days.

This patent is subject to a terminal disclaimer.

(21) Appl. No.: 12/940,495

(22) Filed: Nov. 5, 2010

(65) Prior Publication Data

US 2011/0052721 A1 Mar. 3, 2011

Related U.S. Application Data

(63) Continuation of application No. 11/869,966, filed on Oct. 10, 2007, now Pat. No. 7,906,138.

(60) Provisional application No. 60/850,572, filed on Oct. 10, 2006.

(51) Int. Cl.
  *A61K 9/00* (2006.01)
(52) U.S. Cl.
  USPC ......... 424/438; 424/78.07; 424/407; 514/492
(58) Field of Classification Search
  None
  See application file for complete search history.

(56) References Cited

U.S. PATENT DOCUMENTS

| | | |
|---|---|---|
| 3,137,623 A | 6/1964 | Gessler |
| 3,210,248 A | 10/1965 | Feldmann |
| 3,252,859 A | 5/1966 | Silver et al. |
| 3,326,808 A | 6/1967 | Noseworthy |
| 3,535,427 A | 10/1970 | Millar et al. |
| 3,728,449 A | 4/1973 | Cantor et al. |
| 3,912,806 A | 10/1975 | Dowrick et al. |
| 4,034,099 A | 7/1977 | Bryan |
| 4,049,830 A | 9/1977 | Pugliese |
| 4,140,766 A | 2/1979 | Kalogris |
| 4,199,602 A | 4/1980 | Lentsch |
| 4,258,056 A | 3/1981 | Lentsch |
| 4,344,967 A | 8/1982 | Easton et al. |
| 4,401,666 A | 8/1983 | Wedig et al. |
| 4,435,583 A | 3/1984 | Rogers et al. |
| 4,610,993 A | 9/1986 | Wedig et al. |
| 4,804,530 A | 2/1989 | Sampathkumar |
| 6,187,800 B1 | 2/2001 | Suri et al. |
| 6,254,881 B1 * | 7/2001 | McNally et al. ............... 424/438 |
| 7,087,190 B2 | 8/2006 | Hei et al. |
| 2004/0197422 A1 | 10/2004 | Dorgan |
| 2005/0191270 A1 * | 9/2005 | Gruening et al. ............ 424/78.3 |

FOREIGN PATENT DOCUMENTS

| | | |
|---|---|---|
| GB | 1441747 | 7/1976 |
| GB | 2273441 A | 6/1994 |
| WO | WO 94/13261 | 6/1994 |
| WO | WO 03/057233 A1 | 7/2003 |

OTHER PUBLICATIONS

STN online, file CAPLUS, Acc. No. 1927:33388, Doc. No. 21:33388 (Leitch, Black spot in cheese, Scottish J. Agr. (1927), vol. 10, pp. 165-171), Abstract.*
Rankin, Orbeseal residuals (Feb. 11, 2010), pp. 1-12.*
Hood et al., A colour defect of cheddar cheese, Ottawa-Department of Agriculture (1929), pp. 1-15, Fig. 1-6.*
Arfi et al., "Production of volatile compounds by cheese-ripening yeasts: requirement for a methanethiol donor for S-methyl thioacetate synthesis by *Kluyveromyces lactis*," *Appl. Microbiol. Biotechnol.* (2002) 58:503-510.
Burbank et al., "Volatile sulfur compounds in Cheddar cheese determined by headspace solid-phase microextraction and gas chromatograph-pulsed flame photometric detection," *J. Chromotography A* (2005) 1066:149-157.
Crandall et al., "Antimicrobial Treatment Strategies for Streptococcal and Staphylococcal Mastitis," NMC Annual Meeting Proceedings (2005) 215-216.
Godden et al., "Effectiveness of an Internal Teat Seal in the Prevention of New Intramammary Infections During the Dry and Early-Lactation Periods in Dairy Cows when used with a Dry Cow Intramammary Antiobiotic," *J. Dairy Sci.* (2003) 86:3899-3911.
Lay et al., "Hot Topic: Black Spot Defect in Cheddar Cheese Linked to Intramammary Teat Sealant," J. Diary Sci. (2007) 90:1-4.
Todhunter et al., "Environmental Streptococcal Intramammary Infections of the Bovine Mammary Gland," *J. Dairy Sci.* (1995) 78:2366-2374.
Wilkinson, Ann. "To Seal or Not to Seal: Internal Teat Sealant Strategies," NMC Regional Meeting Proceedings (2003) 16-20.
Wilson et al., "Efficacy of florfenicol versus clinical and subclinical cases of bovine mastitis," *National Mastitis Council Proceedings* (1996) 164-165.
Woolford et al., "The prophylactic effect of a teat sealer on bovine mastitis during the dry period and the following lactation," *New Zealand Veterinary Journal* (1998) 46:12-19.
Zhang, B. et al., "Biomolecule-Assisted Synthesis and Electrochemical Hydrogen Storage of $Bi_2S_3$ Flowerlike Patterns with Well-Aligned Nanorods," *J. Phys. Chem. B* (2006) 110:8978-8985.
Zhang, W. et al., "Low temperature growth of bismuth sulfide nanorods by a hydrothermal method," *Solid State Comm.* (2001)119:143-146.

* cited by examiner

*Primary Examiner* — Abigail Fisher
*Assistant Examiner* — Frank Choi
(74) *Attorney, Agent, or Firm* — Joseph T. Leone, Esq.; Daniel A. Blasiole; DeWitt Ross & Stevens S.C.

(57) ABSTRACT

Described is an intra-mammary teat sealant and a corresponding method of forming a physical barrier in the teat canal of a non-human animal for prophylactic treatment of mammary disorders during the animal's dry period. The method includes the step of infusing a bismuth-free teat seal formulation into the teat canal of the animal. The method also prevents the formation of black spot defect in dairy products, especially cheddar cheese, made from the milk of animals so treated.

6 Claims, 4 Drawing Sheets ically low: 46% for *Streptococcus* spp., 21% for *Staphylococcus* spp., and only 9% for *Staphylococcus aureus* mastitis.
INTRA-MAMMARY TEAT SEALANT FORMULATION AND METHOD OF USING SAME TO REDUCE OR ELIMINATE VISUAL DEFECTS IN AGED CHEESES

CROSS-REFERENCE TO RELATED APPLICATIONS

This is a continuation of application Ser. No. 11/869,966, filed Oct. 10, 2007 now U.S. Pat. No. 7,906,138, which claims priority to provisional application Ser. No. 60/850,572, filed Oct. 10, 2006, incorporated herein by reference.

FIELD OF THE INVENTION

The invention is directed to a bismuth-free, metal-containing, intra-mammary teat sealant to prevent mastitis in dry cows. The intra-mammary teat sealant does not cause visual defects in dairy foods (especially cheese) made from milk from treated animals. The invention is further directed to a method to prevent "black spot defect" (BSD) in cheese.

BACKGROUND

Mastitis in dairy herds is one of the most costly and difficult diseases encountered by dairy producers. Conventional therapies aimed at curing clinical mastitis include intra-mammary antimicrobial therapy. Despite the commercial availability of numerous intra-mammary antimicrobial products, cure rates for clinical mastitis remain perplexingly low: 46% for *Streptococcus* spp., 21% for *Staphylococcus* spp., and only 9% for *Staphylococcus aureus* mastitis. See Wilson et al. (1996) *National Mastitis Council Proceedings* 164-165, and Crandall et al. (2005) *NMC Annual Meeting Proceedings* 215-216. Thus, dairy producers often manage the disease simply by culling mastitis-prone animals from their herds.

Because of the difficulty in treating mastitis, prevention of new intra-mammary infections is a major focus in the dairy industry. The rate of new infections is significantly higher during the dry period as compared to new infections during the lactating period. (For example, one study showed that 61% of all new gram-negative intra-mammary infections occurred during the dry period. See Todhunter et al. (1995) *J. Dairy Sci.* 78:2366.) The three-week period immediately following dry off; and the two weeks prior to calving, are periods particularly prone to new infections. Thus, in recent years dairy producers have focused a considerable amount of effort in "preventive maintenance" of cows during their dry period.

In April of 2003, an internal (or "intra-mammary") teat sealant (ITS) for use in dry cows was introduced in the US market. Marketed in the US under the "ORBESEAL" trademark (US Trademark Registration Nos. 2,772,198 and 3,120,693), the product was developed in New Zealand. The "ORBESEAL"-brand ITS introduced into the US market contains 65% w/w bismuth sub-nitrate dispersed in a viscous paste. The ITS product does not contain any antibiotics, nor does the product contain any active antimicrobial agents. The ITS is injected into the teat end using a tubular applicator syringe, in the same fashion as applying a dry cow antibiotic. The ITS product fills the fissures and folds of the teat canal, thereby creating a physical barrier to pathogens. See U.S. Pat. No. 6,254,881, issued Jul. 3, 2001, incorporated herein by reference.

Initial studies of the "ORBESEAL"-brand product in New Zealand concluded that the product functioned as well as a broad spectrum, long-acting intra-mammary antibiotic in preventing new intra-mammary infections at calving and in preventing clinical appearance of mastitis through the first five (5) months of lactation. See Woolford et al. (1998) *New Zealand Veterinary Journal* 46:1. A more recent study in the US also concluded that this ITS product improved the udder health of cows already infused with cloxacillin benzathine. See Godden et al. (2003) *J. Dairy Sci.* 86:3899-3911. Thus, the "ORBESEAL"-brand ITS has proven to be an effective tool in reducing the number of new cases of mastitis in dairy cows during their dry period. Despite its relatively recent introduction into the US market, the "ORBESEAL"-brand product has enjoyed widespread market acceptance and is used extensively in US dairy herds. In short, the "ORBESEAL"-branded product is very good for its intended purpose of preventing mastitis.

Subsequent to the introduction of the "ORBESEAL"-brand ITS product in the US, a visual defect in aged dairy products, most notably aged cheddar cheeses, began to appear. The visual defect takes the form of small, black spots (roughly 0.5 to 5 mm in diameter) that appear throughout the aged cheese. The spots are a purely aesthetic, visual defect that lowers the graded quality (and hence the market value) of the cheese affected with the problem. The spots are not accompanied by any organoleptic defect in the cheese. Cheese affected with the black spots is saleable, albeit at a lower grade than unaffected cheeses. The defect has been termed "black spot defect" (BSD).

SUMMARY OF THE INVENTION

A first version of the invention is directed to a method of forming a physical barrier in the teat canal of a non-human animal for prophylactic treatment of mammary disorders during the animal's dry period and simultaneously preventing BSD in dairy products made with the animal's milk. The method comprises infusing teat seal formulation into the teat canal of the animal, wherein the teat seal formulation is bismuth-free. The formulation is administered in an amount sufficient to form a physical barrier to entry of microorganisms into the teat, but does not cause black spot defect in diary products made with milk from the animal. The preferred embodiment of the method comprises infusing a teat seal formulation comprising a bismuth-free, non-toxic heavy metal salt in a gel base. Preferably, the teat sealant is devoid of anti-infective agents (i.e., the teat sealant preferably does not contain antibiotics or other anti-infective active agents). Preferably the method comprises infusing a teat seal formulation comprising at least about 30% by weight of the bismuth-free, non-toxic heavy metal salt, more preferably about 50% to about 75% by weight of the bismuth-free, non-toxic heavy metal salt, and more preferably still about 65% by weight of the bismuth-free, non-toxic heavy metal salt. The purpose of the salt is primarily to impart sufficient density to the composition so that the ITS "settles" into the teat canal. In one version of the method, the non-toxic heavy metal salt is selected from the group consisting of titanium dioxide, zinc oxide, barium sulfate and combinations of these salts.

The gel base can be any suitable gel formulation, a host of which are known in the pharmaceutical arts. The preferred gel base comprises aluminum stearate and liquid paraffin (e.g. mineral oil, white petrolatum, yellow petrolatum, etc.). Typical gel bases include a wax or oil of some type, and a salt such as aluminum or magnesium stearate.

Another version of the invention is directed to an intra-mammary teat sealant comprising, in combination, a gel base, and a non-toxic heavy metal salt dispersed in the gel base, wherein the heavy metal salt is devoid of bismuth. As noted earlier, the teat sealant preferably comprises at least about 30% by weight, more preferably about 50% to about 75% by weight, and more preferably still about 65% by weight of the heavy metal salt. The heavy metal salt preferably is titanium dioxide, zinc oxide, barium sulfate or a combination of the same. The gel base preferably comprises aluminum stearate and liquid paraffin.

Yet another version of the invention is an improvement to intra-mammary teat sealants. Specifically, in a method of forming a physical barrier in the teat canal of a non-human animal for prophylactic treatment of mammary disorders during the animal's dry period, wherein the method comprises the step of infusing a seal formulation into the teat canal of the animal without an anti-infective agent, the improvement of the present invention comprises infusing a teat seal formulation comprising a bismuth-free, non-toxic heavy metal salt(s) in a gel base. The improvement prevents the formation of black spot defect in dairy products made from the milk of treated animals.

BRIEF DESCRIPTION OF THE DRAWINGS

FIG. 1A shows the surface of the block, with a black spot defect readily visible. FIG. 1B is a magnified view (with a superimposed ruler) showing the dimensions of the defect. Such spots are equally distributed throughout the cheese.

In FIG. 4A, the various components of "ORBESEAL"-brand intra-mammary teat sealant (ITS) were blended with cheese and each spot was photographed immediately. FIG. 4B shows the same spots photographed after exposure either to volatiles from aged cheddar cheese or hydrogen sulfide gas. Sites 4 and 5 contain bismuth subnitrate and the intact "ORBESEAL"-brand ITS formulation, respectively.

DETAILED DESCRIPTION OF THE INVENTION

Starting in late 2003, a number of inquiries have been made by cheese makers to the University of Wisconsin-Madison, Department of Food Science and Center for Dairy Research (CDR), seeking information about the appearance of a novel "black spot defect" in aged cheeses, notably aged cheddar cheese. Historically, grey to black discolorations in cheese have been the result of several different and distinct causes, including the growth of specific microorganisms (e.g., certain environmental propionibacteria or molds) or the contamination of cheese with food-grade lubricant debris. The particular BSD noted by the cheese makers, however, did not fit the profile of a bacterial contaminant or other spoilage organism, nor did it appear to be lubricant debris that had found its way into the milk stream or other debris introduced during the cheese-making process.

Thus, the first step was to determine the chemical structure of the black spot defect. A great deal of effort was initially made to extract the affected regions of BSD cheese. Extraction efforts using a wide spectrum of organic solvents of varying polarity, hydrophobicity, etc., proved fruitless as a means of isolating any type of organic pigment mass from the cheese matrix. Although extraction of the BSD with organic solvents was not successful, the extraction efforts did yield useful data. Notably, because the pigment did not dissolve or diffuse into such solvents, it could be concluded (with a high degree of probability) that the black spot pigment likewise would not dissolve or diffuse within the cheese matrix itself.

Figure 1A:
FIGS. 1A and 1B are photographs of a typical black spot defect in an 18 kg block of aged white cheddar cheese.
Figure 1B:
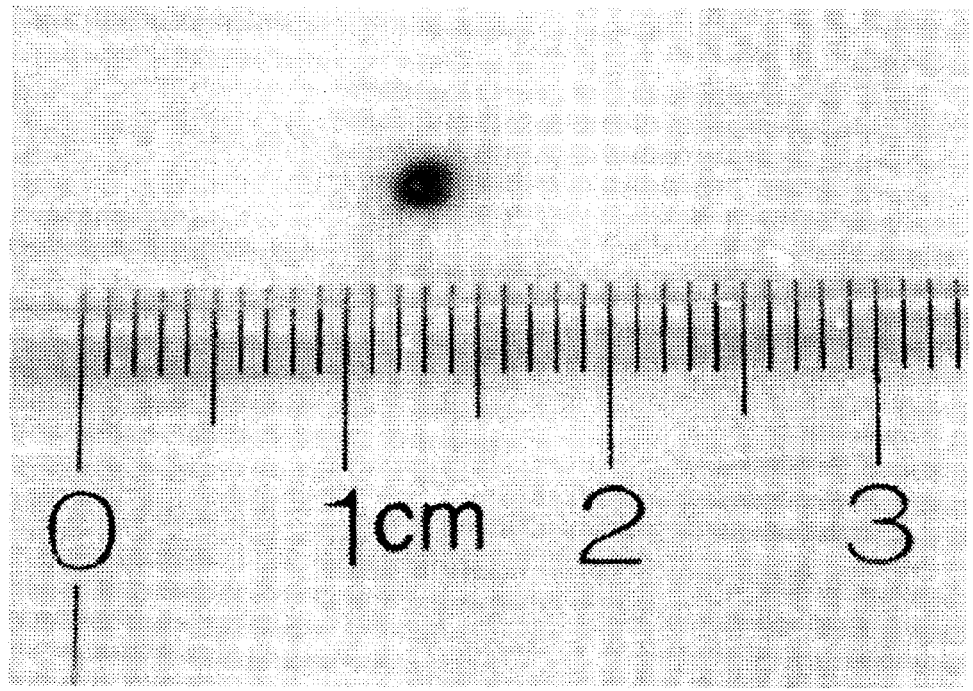

Visual examination of a growing number of cheese samples exhibiting the defect (samples accumulated from commercial cheese makers) confirmed this conclusion—the black spot pigment is well contained and does not appear to diffuse into the cheese matrix. See FIGS. 1A and 1B, which are photographs of a typical 18 kg block of aged, white cheddar cheese affected with the BSD. FIG. 1A is a photograph of the outer surface of the cheese block. FIG. 1B is a magnified view of a single black spot, with a ruler superimposed on the image to show the dimensions of the spot. Spots such as the one shown in FIGS. 1A and 1B typically are equally distributed throughout the cheese block, ranging in size from <1 mm to about 5 mm in diameter. The frequency of the spots within any given 18 kg cheese block varies widely, from <10 per block to well over 100.

There were some anecdotal reports received from cheese makers that specific aging and storage strategies might aid in dissolving or diffusing the spots to the point that they are no longer visually noticeable. (Because the defect is not accompanied by any organoleptic deficiency, "fading" the spots would ameliorate the condition.) Such an effect, however, is highly unlikely given the stability of the pigment to the organic solvents employed in the extraction efforts. In short, the extraction experiments performed by the present inventor used solvents having hydrophobicities similar to milk fat. If the black spot pigment dissolved or diffused into the cheese matrix itself (via an aging or storage protocol), the pigment should likewise readily dissolve or diffuse into an organic solvent having physical characteristics similar to milk fat. That result did not occur in the lab. Moreover, given the typical pH/acidic environment in cheese, and the typical aging/shelf life periods associated with most aged cheddar-type cheeses (0.5 to 2 years), the anecdotal evidence that the defect can be ameliorated via aging or storage protocols is without merit.

One experiment, however, proved most enlightening: the black spot pigment is readily dissolved in nitric acid. This strongly suggested that the pigment was an inorganic salt. Coupled with the timing of the first appearance of the defect, a working hypothesis was formulated, namely that the ITS was either a causative agent of (or at least correlated with) the BSD. The discovery that the black spot pigment readily dissolves in acid supported a further hypothesis that the pigment may be comprised of bismuth III sulfide. Thus, it was concluded the "ORBESEAL"-brand product, which in the US contains 65% by weight of a bismuth-containing salt, was likely being inadvertently introduced into the milk stream. As noted above, the "ORBESEAL"-brand product has been commercially successful because it forms a tight physically barrier to the entry of pathogens into the teat canal. However, removing the product from a treated animal requires stripping of the animal's teats. It appeared that some of the ITS remained in the teats after stripping and was finding its way into the cheese milk.

The next phase of research operated pursuant to a hypothesis that bismuth III sulfide was in fact the causative agent of the BSD. Bismuth subnitrate itself is white and relatively chemically inert. Thus, its trace presence in fluid milk, mozzarella cheese, and yogurt is not readily apparent visually. However, in aged cheeses with high flavor intensity, the black spot defect appears prominently. Thus, it was hypothesized that bismuth III sulfide (a black, relatively insoluble salt) was the product of a reaction between bismuth subnitrate (from the ITS) and hydrogen sulfide produced within the aging cheese by the actions of ripening microflora, enzymes, and certain cofactors acting on the protein/amino acid components of cheese.

In short, the hypothesis was that bismuth subnitrate made its way into the milk stream due to incomplete removal of the ITS prior to milking. The bismuth subnitrate then reacted with hydrogen sulfide to yield bismuth III sulfide according to Equation 1

$$4BiNO_3(OH)_2BiO(OH)+H_2S \rightarrow Bi_2S_3(\text{insol.}, \text{black}) \qquad (\text{Eq. 1})$$

The product, bismuth III sulfide (or simply bismuth sulfide) is a relatively insoluble, black salt.

In addition to having a specific elemental target, bismuth, it was hypothesized that, under the conditions or chemical environment present within the cheese matrix, the $Bi_2S_3$ molecules would form a crystalline structure referred to in the literature as nanorods or nanowhiskers. See W. Zhang et al. (2001) *Sol. State Comm.* 119:143-146 and B. Zhang et al. (2006) *J. Phys. Chem.* 110:8978-8985. These bismuth-containing nanorods would thus constitute light-diffracting particles capable of imparting the grey to black hue seen in the black spot defect.

Efforts were then focused on confirming: 1) the elemental presence of bismuth in the black spot defects; and 2) confirming the physical presence of bismuth III sulfide nanorod structures within the black spot defects.

Confirming the presence of bismuth within the black spots was investigated using inductively coupled plasma mass spectroscopy (ICPMS). AOAC International (Association of Analytical Communities) method 993.14 was used. The first efforts screened multiple black spots for the presence of several elements that could be contributing to BSD. The initial experiments focused on metal salts/oxides typical of those found in milk- and cheese-handling/conveying equipment, and other residual metal derivatives present in food-grade processing. As a measure of control, cheese compositional analyses were conducted. Specifically, protein, ash, and moisture were measured using methods 2001.14, 935.42, and 926.08, of the Official Methods of Analysis, AOAC 17$^{th}$ Edition, respectively (copyright 2000, ISBN: 0935584-67-6). Fat was measured according to the method described in the Official Methods of Analysis, AOAC 17th Edition.

Transmission electron microscopy (TEM) studies were performed as follows: approximately 100 µl double-distilled water was added to samples and the mixture was pulverized into a suspension with a glass rod. Approximately 5 µl aliquots of suspended sample were deposited onto polyvinyl alcohol-formaldehyde acetal-coated 300 mesh copper TEM grids (Ted Pella, Inc., Redding, Calif.). Excess sample was wicked away with small sections of filter paper and the remaining sample was dried to the surface of the grid at room temperature. In some cases, NANO-W-brand TEM negative stain (Nanoprobes, Incorporated, Yaphank, N.Y.) was applied over the dried sample to enhance contrast and visibility. Specimens were observed with a Philips CM 120 electron microscope and images were collected with a MegaView 3 Digital camera (from SIS, Ringoes, N.J.). Measurements were taken with SIS-brand analysis software (Ringoes, N.J.) calibrated with reference samples of known lengths.

ICPMS results demonstrated the presence of the elements chromium, copper, iron, nickel, and bismuth in the BSD region. Although incremental increases in the elements chromium, copper, iron, and nickel were found, bismuth concentrations in the BSD region were routinely three orders of magnitude greater than the same cheese assayed in non-BSD areas. These results show that bismuth is the only element present in sufficient quantities to participate in a pigment-generating reaction.

Figure 2:
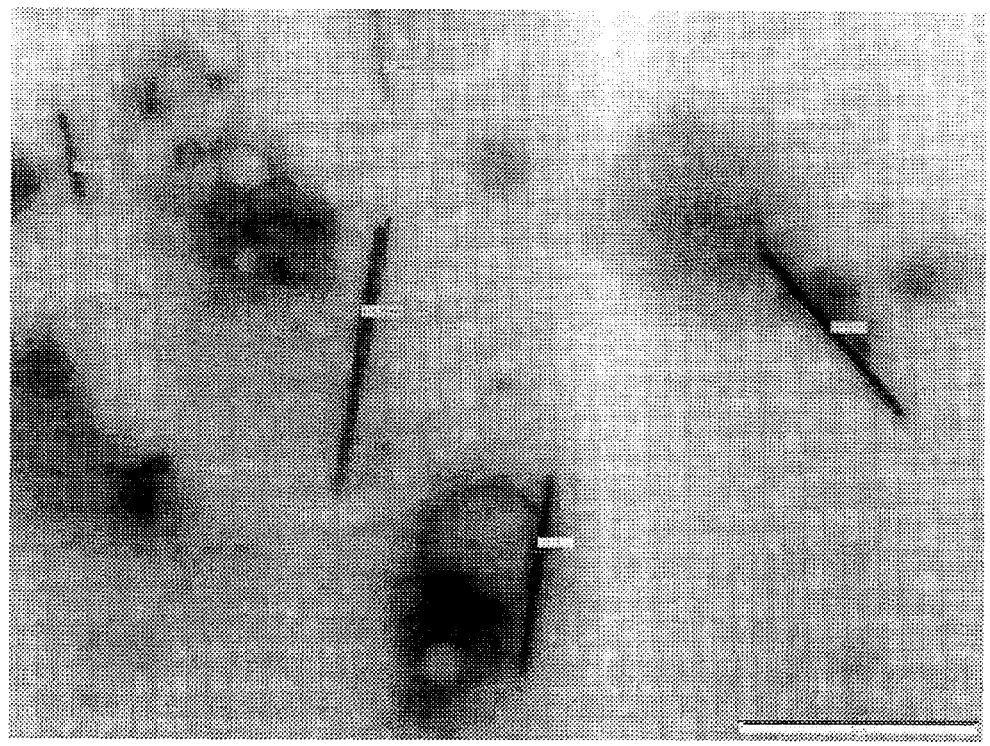
FIG. 2 is an electron photomicrograph of a black spot defect exhibiting characteristic hair- or rod-like structures of bismuth (III) sulfide nanorods. No such structures appeared in any non-BSD cheeses or non-BSD cheese regions tested. The rods shown in FIG. 2 have diameters ranging from 37.09 nm to 129.33 nm.
Figure 3:
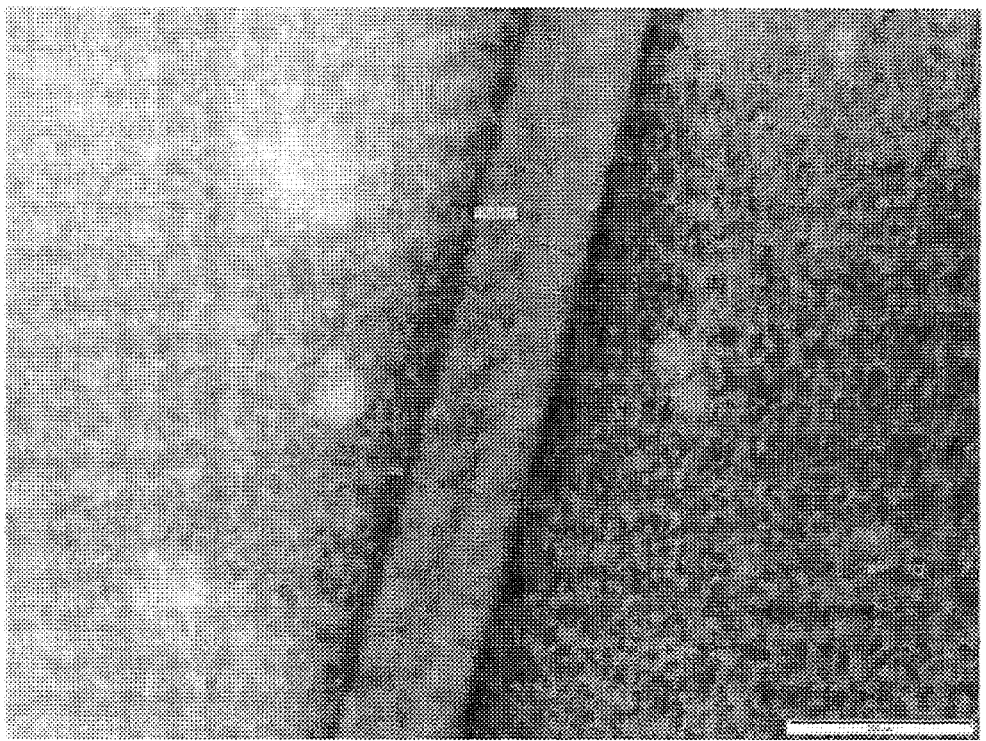
FIG. 3 is an electron photomicrograph of a single rod-like structure from a black spot defect region. The rod shown in 130.88 nm in diameter and exhibits a line bisecting the length of the rod.

Several hundred TEM images of BSD regions of cheese samples were captured with a single, consistent conclusion. Nanorods typical of those reported in the literature cited above were uniquely present in the BSD cheese region. An example of such an image is presented in FIG. 2. The nanorod structures shown in FIG. 2 are too small to be readily detected with a light microscope. The nanorods shown in FIG. 2 range in diameter from about 69 nm to about 130 nm. The nanorods are very stable to the potentially abusive conditions of TEM. The rods appear to have a slightly mottled surface and they exhibit a characteristic line running the length of the nanorod. See FIG. 3, which is an increased magnification view of a single nanorod. The presence of such structures is consistent with the presence of bismuth sulfide nanorods formed under the conditions present in the cheese matrix.

Figure 4A:
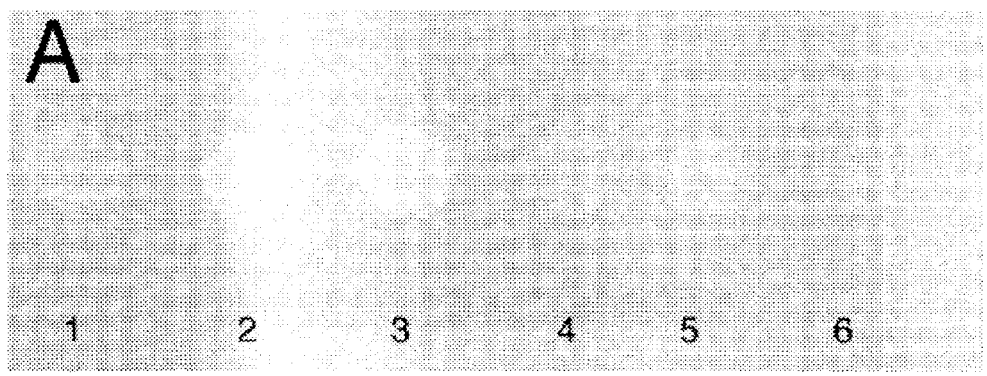
FIGS. 4A and 4B are images of laboratory-induced black spot defects.
Figure 4B:
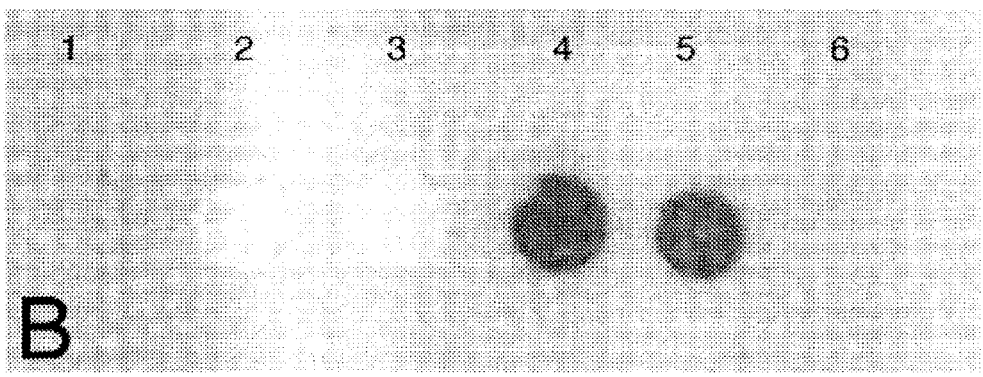

To confirm the reactivity of bismuth subnitrate as a reactant in forming bismuth III sulfide nanorods, additional assays were conducted to see if BSD could be purposefully recreated in the lab. In short, cheeses were manufactured with known amounts of ITS components and subjected to either the authentic volatile gasses produced by maturing cheeses or exposed directly to the hypothesized bismuth subnitrate co-reactant, hydrogen sulfide gas. In both situations, the responses were invariably the same: When cheese samples containing bismuth subnitrate or the complete ITS formulation were exposed to authentic cheese volatiles or to "chemical standard"-grade $H_2S$ gas, each formed identical black pigmentation with the accompanying presence of nanorod structures, further confirming that bismuth subnitrate is the culprit in BSD. The results are shown in FIG. 4. No other ITS component formed black spots when so exposed. Furthermore, the susceptible sites formed identically black pigmentation when exposed to either authentic cheese volatiles or to hydrogen sulfide gas, thus confirming that hydrogen sulfide gas was the suspected co-reactant.

From a cheese manufacturing and aging or ripening standpoint, it is not reasonable to consider targeting the elimination of hydrogen sulfide gas production as a means of controlling BSD. Hydrogen sulfide is a highly aroma active compound, the product of microbial, enzymatic and co-factor activities against sulfur-containing amino acids such as cysteine. See Arfi et al., (2002) *Appl. Microbiol. Biotechnol.* 58:503-510. There is ample research to support the claim that hydrogen sulfide gas is a necessary and/or valued component of typical aged cheddar cheese flavor. See Burbank & Qian (2005) *J. Chrom.* 1066:149-157. Even if a scheme was devised to eliminate the production of hydrogen sulfide (by interrupting of dozens of complex metabolic pathways) the resulting final product runs the risk of a flavor character unacceptable to cheese graders and consumers.

Thus, in the present invention, the formulation of the ITS is altered to exclude bismuth-containing salts. As shown in the above experiments, it is the bismuth subnitrate in the commercially-available ITS that give rise to the BSD. Thus, using an ITS that does not contain bismuth, nor any other heavy metal salt that reacts with hydrogen sulfide to yield a dark, insoluble pigment, eliminates the BSD.

EXAMPLES

The following Examples are included solely to provide a more complete description of the invention disclosed and claimed herein. The Examples do not limit the invention in any way.

Example 1

A test ITS according to the present invention was formulated. The test ITS was identical to the "ORBESEAL"-brand formulation, with the exception that it did not contain any bismuth or bismuth-containing salts. The test ITS comprised zinc oxide, titanium dioxide, mineral oil (30-40%), and aluminium stearate.

To prepare a batch of ITS, liquid paraffin (e.g., mineral oil) is delivered into a suitable vessel equipped with a mixer. Aluminum stearate is added and the mixture is stirred and heated to about 160° C. until homogeneous (about two hours). The non-toxic, non-bismuth containing salt is then added in portions to the mixture, with stirring, until the desired amount of metal salt has been added. The mixture is then stirred until homogenous. The products is then transferred into conventional injector tubes for intra-teat administration.

Example 2

The object of this Example was to compare retention within the teats of non-lactating dairy cows of an ITS according to the present invention as compared to the "ORBESEAL"-brand product.

The study was performed at the Blaine Dairy of the University of Wisconsin-Madison (UW), in Arlington, Wis. Sixteen (16) cows (n=64 teats) were enrolled on the day of dry off. All enrolled cows were required to have four functional quarters and no visible sign of mastitis. All cows were dried off and received intramammary antibiotic dry cow therapy (DCT) according to standard UW dairy herd protocols. Parity and milk yield (at dry off) were recorded for each cow. Upon initial enrolment, teats were scored for shape, length, diameter and degree of teat end hyperkeratosis. Within each cow, two teats were assigned to receive the "ORBESEAL"-brand ITS and two teats were assigned to receive the test ITS. The administration protocol was designed to ensure that each product was administered uniformly among teat locations, eight teats each per product administered in each location (right-rear, right-front, left-rear, left-front). Sealant tubes were weighed before and after administration to determine the net volume administered. Prior to receiving DCT & the internal teat sealant, teat ends were cleaned using a single 70% isopropanol alcohol wipe and partial insertion technique was used to reduce the probability of introducing teat skin pathogens. After administration of the internal sealant, teats were dipped with an external teat disinfectant.

Teats were examined on Days 1, 2, 3, 4, 5, 6, 7, 14, 28, 42 and at calving to detect redness, swelling and/or sealant leakage. On Days 14, 28, 42 and at calving, sealant was removed from one teat (eight teats for each sealant per removal day) of each cow by hand stripping. The removed sealant was collected with the first milk into graduated 50 ml plastic vials. The vials were centrifuged (3000 rpm×5-7 minutes), the supernatant rinsed, and the recovered sealant weighed. The amount of recovered sealant was compared at each period between the test ITS-treated teats and the "ORBESEAL"-brand ITS-treated teats. Follow up samples were collected at Day 1 post-calving using the same procedure. At all sampling periods, after removal of the sealant, teats were dipped with an external teat disinfectant. After calving, quarter milk samples were aseptically collected from all quarters and cultured to identify intramammary infections.

Group Characteristics—Teat Length and Volume:

A total of 16 cows were enrolled into the study for a total number of 64 teats; 32 teats received the test ITS and 32 teats received the "ORBESEAL"-brand ITS. The teat length and volume for the test population is shown in Table 1:

TABLE 1

Mean, Standard Deviation, and Standard Errors for Teat Length and Volume by Compound

| | Group A ("ORBESEAL"-ITS) | | | | Group B (Test ITS) | | | | |
|---|---|---|---|---|---|---|---|---|---|
| | N | Mean | S.D. | S.E. | N | Mean | S.D. | S.E. | P |
| Length | 32 | 5.12 | 0.88 | 0.16 | 32 | 5.11 | 0.86 | 0.15 | 0.95 |
| Volume | 32 | 23.60 | 8.61 | 1.52 | 32 | 25.72 | 9.73 | 1.73 | 0.36 |

There was no significant difference in teat length or volume for teats in Group A or Group B (p>0.36). Overall teat length was 5.11 cm, ranging from 3.3 cm to 7.3 cm. The average teat length was 5.12 cm for Group A and 5.11 cm for Group B, and ranged from 3.3 cm to 7.3 cm for Group A and from 3.5 cm to 7.10 cm for Group B. A two Sample paired t-test was performed to test the null hypothesis that the mean teat length in the two treatment group did not differ. There was no significant difference in teat length between teats randomized to receive either product (p=0.95).

The overall teat volume was 24.66 $cm^3$, ranging from 12.47 $cm^3$ to 54.34 $cm^3$ (std. dev. 9.17 $cm^3$). The mean teat volume was 23.6 $cm^3$, ranging from 12.54 $cm^3$ to 54.34 $cm^3$ (std. dev. 8.60 $cm^3$) in Group A. In Group B, mean teat volume was 25.71 $cm^3$, ranging from 12.47 $cm^3$ to 48.25 $cm^3$ (std. dev. 9.73 $cm^3$). A two sample paired t-test was used to test the null hypothesis that the teat volume in the two groups did not differ. There was no significant difference in teat volume between teats randomized to receive either product (p=0.95 and p=0.35; log transformed analysis).

Hyperkeratosis: Teat-end health was scored for hyperkeratosis using the following scale: No ring (N), Smooth Ring (S), Rough (R), Very Rough (VR). The distribution of teat scores was: N (n=21; 32.8%), S (n=31; 48.4%), R (n=11; 17.2%) and VR (n=1, 2%). An $X^2$ test confirmed that the distribution of hyperkeratosis score was not associated with treatment group (p=0.13).

TABLE 2

Descriptive Statistics for Hyperkeratosis

| | Group A ("ORBESEAL" ITS) | | Group B (Test ITS) | | Overall | |
|---|---|---|---|---|---|---|
| Score | Frequency | Percent | Frequency | Percent | Frequency | Percent |
| N | 13 | 40.63 | 8 | 25.00 | 21 | 32.81 |
| S | 11 | 34.38 | 20 | 62.50 | 31 | 48.88 |
| R | 7 | 12.88 | 4 | 12.50 | 11 | 17.19 |
| VR | 1 | 3.23 | n/a | n/a | 1 | 1.56 |

Amount of Sealant Administered, Recovered and Lost: Statistical analyses using a paired t-test were performed to determine if the amount of sealant administered, recovered, or lost (not recovered) did not differ based on treatment group.

TABLE 3

Two Sample Paired t-Test for the Mean of Administered, Recovered and Lost Sealant by Product

| Group A ("ORBESEAL" ITS) | | | Group B (Test ITS) | | | Overall | | | |
|---|---|---|---|---|---|---|---|---|---|
| N | Mean | S.D. | N | Mean | S.D. | N | Mean | S.D. | P |
| Administered | | | | | | | | | |
| 32 | 3.46 | 0.85 | 32 | 3.77 | 0.96 | 64 | 3.62 | 0.91 | 0.12 |
| Recovered | | | | | | | | | |
| 32 | 0.85 | 1.42 | 32 | 0.79 | 1.57 | 64 | 0.82 | 1.49 | 0.89 |
| Lost | | | | | | | | | |
| 32 | 2.71 | 1.37 | 32 | 3.04 | 1.55 | 64 | 2.88 | 1.46 | 0.40 |

Of the four (4) grams in each tube, the overall amount of sealant administered was 3.62 grams. There was no significant difference in the amount of "ORBESEAL"-brand ITS (3.46 gram) or test ITS (3.62) administered (P=0.12).

Overall, the amount of sealant recovered was 0.82 gram and there were no significant differences based on treatment (P=0.89). The overall amount of sealant lost was 2.88 grams and did not differ by treatment group (P=0.40). The amount of sealant recovered tended to be associated with recovery date (P=0.08) with more sealant recovered on day 14 as compared to other recovery periods (day 14, recovery=1.6 grams; day 28 recovery=0.68 grams; day 42 recovery=0.65 grams; calving recovery=0.33 grams).

Simple linear regression was used to determine that there was no significant relationship between the amount of administered sealant and teat volume (p=0.59, p=0.53).

For the recovered sealant a simple linear regression test was performed to test the null hypothesis that there was no significant linear relationship between the amount of recovered sealant and the teat volume. Only 6% of the recovered sealant was accounted for by teat volume (P=0.05).

The proportion of administered sealant was not significantly associated with teat volume, while the recovered sealant was correlated significantly with the teat volume but only for a small proportion (6%).

A one-way ANOVA was used to determine univariate relationships between the amount of administered and recovered sealant and the teat position, the product, the cow.

TABLE 4

Administered and Recovered Volume Univariate Association Table (P values)

| | Administered (p) | Recovered (p) |
|---|---|---|
| Teat volume | 0.53 | 0.13 |
| Teat position | 0.56 | 0.52 |
| Product | 0.19 | 0.88 |
| Day | — | 0.07 |
| Cow | 0.05 | 0.17 |

What is claimed is:

1. A method of forming a physical barrier in the teat canal of a non-human animal for prophylactic treatment of mammary disorders during the animal's dry period wherein the physical barrier does not cause black spot defect in dairy products made with milk from the animal, the method comprising:
    infusing an amount of a teat seal formulation into the teat canal of the animal, wherein the teat seal formulation comprises at least about 30% by weight of a bismuth-free, non-toxic, inorganic heavy metal salt in a gel base, and wherein the amount is sufficient to form a physical barrier to entry of microorganisms into the teat canal, and wherein the teat seal formulation does not cause black spot defect in aged cheese made with milk from the animal.

2. The method of claim 1, wherein the teat seal formulation is devoid of anti-infective agents.

3. The method of claim 1, wherein the teat seal formulation comprises about 50% to about 75% by weight of the salt.

4. The method of claim 1, wherein the teat seal formulation comprises about 65% by weight of the salt.

5. The method of claim 1, wherein the gel base comprises aluminum stearate.

6. The method of claim 1, wherein the gel base comprises liquid paraffin.

* * * * *